United States Patent
Walcheck et al.

(10) Patent No.: US 12,098,182 B2
(45) Date of Patent: *Sep. 24, 2024

(54) POLYPEPTIDES, CELLS, AND METHODS INVOLVING ENGINEERED CD16

(71) Applicant: Regents of the University of Minnesota, Minneapolis, MN (US)

(72) Inventors: Bruce Kenneth Walcheck, Lino Lakes, MN (US); Dan Samuel Kaufman, Woodbury, MN (US); Jianming Wu, Plymouth, MN (US); Yawu Jing, Shoreview, MN (US); Zhenya Ni, Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1118 days.

This patent is subject to a terminal disclaimer.

(21) Appl. No.: 16/575,624

(22) Filed: Sep. 19, 2019

(65) Prior Publication Data

US 2020/0017570 A1 Jan. 16, 2020

Related U.S. Application Data

(63) Continuation of application No. 15/300,024, filed as application No. PCT/US2015/022998 on Mar. 27, 2015, now Pat. No. 10,464,989.

(60) Provisional application No. 61/971,996, filed on Mar. 28, 2014.

(51) Int. Cl.
| | | |
|---|---|---|
| C12N 15/63 | (2006.01) | |
| A61K 35/17 | (2015.01) | |
| A61K 38/17 | (2006.01) | |
| A61K 39/395 | (2006.01) | |
| C07K 14/735 | (2006.01) | |
| C07K 16/32 | (2006.01) | |
| C12N 5/00 | (2006.01) | |
| C12N 5/0783 | (2010.01) | |
| C12N 5/0786 | (2010.01) | |
| C12N 5/0787 | (2010.01) | |
| A61K 39/00 | (2006.01) | |
| A61K 48/00 | (2006.01) | |

(52) U.S. Cl.
CPC ........ C07K 14/70535 (2013.01); A61K 35/17 (2013.01); A61K 38/1774 (2013.01); A61K 39/39558 (2013.01); C07K 16/32 (2013.01); C12N 5/0642 (2013.01); C12N 5/0645 (2013.01); C12N 5/0646 (2013.01); A61K 2039/505 (2013.01); C07K 2317/76 (2013.01); C12N 2501/599 (2013.01); C12N 2510/00 (2013.01)

(58) Field of Classification Search
CPC .............. C07K 14/70535; A61K 35/17; A61K 39/39558; A61K 2039/505; C12N 5/0642; C12N 5/0646; C12N 2510/00
See application file for complete search history.

(56) References Cited

U.S. PATENT DOCUMENTS

| | | | |
|---|---|---|---|
| 5,998,166 | A | 12/1999 | Luo |
| 7,618,817 | B2 | 11/2009 | Cambell |
| 7,829,084 | B2 | 11/2010 | Ledbetter et al. |
| 10,464,989 | B2 | 11/2019 | Walcheck et al. |
| 2006/0292156 | A1 | 12/2006 | Campbell |
| 2008/0003225 | A1 | 1/2008 | Vie et al. |
| 2009/0196870 | A1 | 8/2009 | Ledbetter et al. |
| 2017/0174743 | A1 | 6/2017 | Walcheck et al. |

FOREIGN PATENT DOCUMENTS

| | | |
|---|---|---|
| CN | 1852976 | 10/2006 |
| CN | 101583625 | 11/2009 |
| CN | 101627054 | 1/2010 |
| CN | 102858985 | 1/2013 |
| EP | 1734119 | 12/2006 |
| JP | 1999-511649 | 10/1999 |
| JP | H11-511649 | 10/1999 |
| JP | 2007-528194 | 3/2007 |
| JP | 2017-511135 | 4/2017 |
| WO | WO 96/34953 | 11/1996 |
| WO | WO 2005/017148 | 2/2005 |
| WO | WO 2005/062929 | 7/2005 |
| WO | WO 2010/040091 | 4/2010 |
| WO | WO 2015/148926 | 10/2015 |

OTHER PUBLICATIONS

Clemenceau et al. The human natural killer cytotoxic cell line NK-92, once armed with a murine CD16 receptor represents a convenient cellular tool for the screening of mouse mAbs according to their ADCC potential. mAbs 5:4, 587-594; (Year: 2013).*

Clemenceau et al. Antibody-dependent cellular cytotoxicity (ADCC) is mediated by genetically modified antigen-specific human T lymphocytes. Blood 107:4669-4677, (Year: 2006).*

(Continued)

*Primary Examiner* — Quang Nguyen

(74) *Attorney, Agent, or Firm* — Fish & Richardson P.C.

(57) ABSTRACT

This disclosure describes, generally, a modified form of CD16, genetically-modified cells that express the modified CD16, and methods that involve the genetically-modified cells. The modified form of CD16 can exhibit increased anti-tumor and/or anti-viral activity due, at least in part, to reduced susceptibility to ADAM17-mediated shedding upon NK cell stimulation.

18 Claims, 9 Drawing Sheets

Specification includes a Sequence Listing.

(56) References Cited

OTHER PUBLICATIONS

Dietrich et al., "Identification of the kinesin KifC3 as a new player for positioning of peroxisomes and other organelles in mammalian cells," Biochimica et Biophysica Acta (BBA)—Molecular Cell Research, 1833(12):3013-24, Dec. 2013.
Gleason et al. Bispecific and trispecific killer cell engagers directly activate human NK cells through CD16 signaling and induce cytotoxicity and cytokine production. Mol. Cancer Ther. 11:2674-2684, (Year: 2012).
Vallera et al. Heterodinneric bispecific single-chain variable-fragment antibodies against EpCAM and CD16 induce effective antibody-dependent cellular cytotoxicity against human carcinoma cells. Cancer Biotherapy and Radiopharmaceuticals 28; doi.org/10.1089/cbr.2012.1329; 20 pages, (Year: 2013).
Alderson et al., "Clinical cancer therapy by NK cells via antibody-dependent cellmediated cytotoxicity," J Biomed Biotechnol., 2011:379123, 2011.
Binyamin et al., Blocking NK cell inhibitory self-recognition promotes antibody-dependent cellular cytotoxicity in a model of anti-lymphoma therapy, J Immunol., 180(9):6392-6401, May 1, 2008.
Bryceson et al. "Synergy among receptors on resting NK cells for the activation of natural cytotoxicity and cytokine secretion," Blood., 107(1):159-166, Jan. 2006.
Bryceson et al., "Molecular mechanisms of natural killer cell activation," J Innate Immun., 3:216-226, 2011.
Caescu et al., "Active-site determinants of substrate recognition by the metalloproteinases TACE and ADAMl O," Biochem J., 424(1):79-88, Oct. 2009.
Choi et al., "Hematopoietic and endothelial differentiation of human induced pluripotent stem cells," Stem Cells., 27:559-567, 2009.
Coxon et al., "Fc gamma Rlii mediates neutrophil recruitment to immune complexes, a mechanism for neutrophil accumulation in immune-mediated inflammation," Immunity., 14(6):693-704, Jun. 2001.
Deguine et al., "Cutting edge: tumor-targeting antibodies enhance NKG2D-mediated NK cell cytotoxicity by stabilizing NK cell-tumor cell interactions," J Immunol., 189(11):5493-5497, Dec. 2012.
Doedens et al., "Stimulation-induced down-regulation of tumor necrosis factor-alpha converting enzyme," J Biol Chem., 275:14598-14607, 2000.
Dong et al., "Fcgamma receptor Illa single-nucleotide polymorphisms and haplotypes affect human IgG binding and are associated with lupus nephritis in African Americans," Arthritis Rheumatol., 66(5):1291-1299, May 2014.
Eguizabal et al., "Natural killer cells for cancer immunotherapy: pluripotent stem cells-derived NK cells as an immunotherapeutic perspective," Front Immunol., 5:439, 2014.
Feehan et al., "Shedding of the lymphocyte L-selectin adhesion molecule is inhibited by a hydroxamic acid-based protease inhibitor. Identification with an L-selectinalkaline phosphatase reporter," J Biol Chem., 271:7019-7024, 1996.
Galon et al., "Identification of the cleavage site involved in production of plasma soluble Fc gamma receptor type III (CD16)," Eur J Immunol., 28:2101-2107, 1998.
Geller et al., "Intraperitoneal delivery of human natural killer cells for treatment of ovarian cancer in a mouse xenograft model," Cytotherapy., 15:1297-1306, 2013.
Gong et al., "Characterization of a human cell line (NK-92) with phenotypical and functional characteristics of activated natural killer cells," Leukemia., 8:652-658, 1994.
Harrison et al., "Involvement of a metalloprotease in spontaneous and phorbol ester-induced release of natural killer cell-associated Fc gamma Rlii (CD 16-11)," J Immunol., 147(10):3459-3465, Nov. 15, 1991.
Hellstrom et al., "Overexpression of HER-2 in ovarian carcinomas," Cancer Res., 61:2420-2423, 2001.
Huizinga et al., "Soluble Fc gamma receptor III in human plasma originates from release by neutrophils," J Clin Invest., 86(2):416-423, Aug. 1990.
International Preliminary Report on Patentability for International Application No. PCT/US2015/022998, issued Oct. 13, 2016, 7 pgs, Considered.
International Search Report and Written Opinion for International Application No. PCT/US2015/022998, issued Jul. 2, 2015; 10 pgs Considered.
Japanese Office Action in Japanese Office Application No. 2016-559573, dated Apr. 9, 2019, 585 pages, Considered.
Jewett et al., "Tumor induced inactivation of natural killer cell cytotoxic function; implication in growth, expansion and differentiation of cancer stem cells, " J Cancer., 2:443-457, 2011.
Jing et al. Identification of an ADAM17 cleavage region in human CD16 (FcgannnnaRIII) and the engineering of a non-cleavable version of the receptor in NK cells. PLOS One; D01:10.1371/journal.pone.0121788, pp. 1-14, (Year: 2015).
Jing et al., "Identification of an ADAMl 7 Cleavage Region in Human CD16 (FcyRIII) and the Engineering of a Non-Cleavable Version of the Receptor in NK Cells," Plos One., 10(3):e0121788, 2015.
Kahn et al., "Membrane proximal cleavage of L-selectin: identification of the cleavage site and a 6-kD transmembrane peptide fragment of L-selectin," J Cell Biol., 125:461-470, 1994.
Kaufman DS., "Toward clinical therapies using hematopoietic cells derived from human pluripotent stem cells, " Blood., 114:3513-3523, 2009.
Kirkwood et al., "Immunotherapy of cancer in 2012," CA Cancer J Clin., 62:309-335, 2012.
Knorr et al., "Clinical-scale derivation of natural killer cells from human pluripotent stem cells for cancer therapy," Stem Cells Transl Med., 2:274-283, 2013.
Knorr et al., "Engineered human embryonic stem cell-derived lymphocytes to study in vivo trafficiking and immunotherapy," Stem Cells and Development., 22:1861-1869, Feb. 19, 2013.
Lai et al., "Alterations in expression and function of signal-transducing proteins in tumor-associated T and natural killer cells in patients with ovarian carcinoma," Clin Cancer Res., 2:161-173, 1996.
Lajoie et al., "ADAM17-mediated shedding of FcgammaRIIIA on human NK cells: identification of the cleavage site and relationship with activation," J Immunol., 192(2):741-751, Jan. 15, 2014.
Lanitis et al., "Primary human ovarian epithelial cancer cells broadly express HER2 at immunologically-detectable levels, " PLOS One., 7:e49829, 2012.
Le Bouteiller et al., "Engagement of CD160 receptor by HLA-C is a triggering mechanism used by circulating natural killer (NK) cells to mediate cytotoxicity," Proc Natl Acad Sci USA., 99(26):16963-16968, Dec. 24, 2002.
Le Garff-Tavernier et al., "Human NK cells display major phenotypic and functional changes over the life span," Aging Cell., 9: 527-535, 2010.
Li et al., "ADAMl17 deficiency by mature neutrophils has differential effects on L-selectin shedding, " Blood., 108:2275-9, 2006.
Lin-Moshier et al., "Re-evaluation of the role of calcium homeostasis endoplasmic reticulum protein (CHERP) in cellular calcium signaling," J Biol Chem., 288:355-367, 2013.
Long et al., "ADAM17 activation in circulating neutrophils following bacterial challenge impairs their recruitment," J Leukoc Biol., 92(3):667-672, Sep. 2012.
Long et al., "In vivo role of leukocyte ADAM17 in the inflammatory and host responses during E. coli-mediated peritonitis," J Leukoc Biol., 87(6):1097-1101, Jun. 2010.
Louis et al., "Cloning and sequencing of the cellular-viral junctions from the human adenovirus type 5 transformed 293 cell line," Virology., 233:423-429, 1997.
Maccio and Madeddu., "Inflammation and ovarian cancer," Cytokine., 58:133-147, 2012.
Matala et al., "The cytoplasmic domain of L-selectin participates in regulating L-selectin endoproteolysis," J Immunol., 167(3):1617-1623, Aug. 1, 2001.

(56) References Cited

OTHER PUBLICATIONS

Mezyk et al., "Structure and functions of tumor necrosis factor-alpha converting enzyme," Acta Biochim Pol., 50:625-645, 2003.
Migaki et al., "Mutational analysis of the membrane-proximal cleavage site of L-selectin: relaxed sequence specificity surrounding the cleavage site," J Exp Med., 182:549-557, 1995.
Miller, "Therapeutic applications: natural killer cells in the clinic," ASH Education Program Book, 2013(1):247-53, Dec. 2013.
Montaldo et al., "Human NK cell receptors/markers: a tool to analyze NK cell development, subsets and function," Cytometry A., 83:702-713, 2013.
Ng et al., "A protocol describing the use of a recombinant protein-based, animal product-free medium (APEL) for human embryonic stem cell differentiation as spin embryoid bodies," Nat Protoc., 3:768-776, 2008.
Ng et al., "Forced aggregation of defined Nos. of human embryonic stem cells into embryoid bodies fosters robust, reproducible hematopoietic differentiation," Blood., 106:1601-1603, 2005.
Ni et al., "Expression of chimeric receptor CD4zeta by natural killer cells derived from human pluripotent stem cells improves in vitro activity but does not enhance suppression of HIV infection in vivo," Stem Cell., 32:1021-1031, 2014.
Ni et al., "Human pluripotent stem cells produce natural killer cells that mediate anti-HIV-1 activity by utilizing diverse cellular mechanisms," J Viral., 85:43-50, 2011.
Nimmerjahn and Ravetch, "Fcgamma receptors as regulators of immune responses," Nat Rev Immunol., 8(1):34-47, Jan. 2008.
Ory et al., "Sequences of complementary DNAs that encode the NAI and NA2 forms of Fc receptor III on human neutrophils," J Clin Invest., 84(5):1688-1691, Nov. 1989.
Ott et al., "Potent, exceptionally selective, orally bioavailable inhibitors of TNF-alpha Converting Enzyme (TACE): novel 2-substituted-1H-benzo[d]imidazol-1-y1)methyl)benzamide Pl' substituents," Bioorg Med Chem Lett., 18:1577-1582, 2008.
Peruzzi et al., "Membrane-type 6 matrix metalloproteinase regulates the activation-induced downmodulation of CD16 in human primary NK cells," J Immunol., 191(4):1883-1894, Aug. 15, 2013.
Peschon et al., "An essential role for ectodomain shedding in mammalian development," Science., 282:1281-1284, 1998.
Ran et al., "RUNX1a enhances hematopoietic lineage commitment from human embryonic stem cells and inducible pluripotent stem cells," Blood., 121:2882-2890, 2013.
Ravetch and Perussia B, "Alternative membrane forms of Fc gamma RIII(CD16) on human natural killer cells and neutrophils. Cell type-specific expression of two genes that differ in single nucleotide substitutions," J Exp Med., 170(2):481-497, Aug. 1, 1989.
Reiss et al., "The "a disintegrin and metalloprotease" (ADAM) family of sheddases: physiological and cellular functions," Semin Cell Dev Biol., 20:126-137, 2009.
Romee et al., "NK cell CD16 surface expression and function is regulated by a disintegrin and metalloprotease-17 (ADAM17)," Blood., 121:3599-3608, 2013.
Selvaraj et al., "The major Fc receptor in blood has a phosphatidylinositol anchor and is deficient in paroxysmal noctural hemoglobinuria," Nature., 333(6173):565-567, Jun. 9, 1988.
Shilov et al., "The Paragon Algorithm, a next generation search engine that uses sequence temperature values and feature probabilities to identify peptides from tandem mass spectra," Mal Cell Proteomics., 6(9):1638-1655, Sep. 2007.
Siegel et al., "Cancer statistics, 2012" CA Cancer J Clin., 62:10-29, 2012.
Stawikowska et al., "Activity of ADAMI 7 (a disintegrin and metalloprotease 17) is regulated by its noncatalytic domains and secondary structure of its substrates," J Biol Chem., 288:22871-22879, Aug. 2, 2013.
Teillaud et al., "Natural and recombinant soluble low-affinity Fc gamma R: detection, purification, and functional activities," Immunomethods., 4(1):48-64, Feb. 1994.
Teillaud et al., "Soluble CD16 binds peripheral blood mononuclear cells and inhibits pokeweed-mitogen-induced responses," Blood., 82(10):3081-3090, Nov. 15, 1993.
Thorp et al., "Shedding of the Mer tyrosine kinase receptor is mediated by ADAM17 protein through a pathway involving reactive oxygen species, protein kinase Cdelta, and p38 mitogen-activated protein kinase (MAPK)," J Biol Chem., 286:33335-33344, 2011.
Tian et al., Bioluminescent imaging demonstrates that transplanted human embryonic stem cell-derived CD34(+) cells preferentially develop into endothelial cells, Stem Cells., 27:2675-2685, 2009.
Tosi and Zakem, "Surface expression ofFc gamma receptor III (CD16) on chemoattractant-stimulated neutrophils is determined by both surface shedding and translocation from intracellular storage compartments," J Clin Invest., 90(2):462-470, Aug. 1992.
Tucher et al., "LC-MS based cleavage site profiling of the proteases ADAM10 and ADAM17 using proteome-derived peptide libraries," J Proteome Res., 13:2205-2214, 2014.
Walcheck et al., "ADAM-17-independent shedding ofL-selectin," J Leukoc Biol., 74:389-394, 2003.
Wang et al., "ADAM17 cleaves CD16b (FcyRlllb) in human neutrophils," Biochim Biophys Acta., 1833(3):680-685, Mar. 2013.
Wang et al., "Different signaling pathways stimulate a disintegrin and metalloprotease-17 (ADAMI 7) in neutrophils during apoptosis and activation," J Biol Chem., 286:38980-38988, 2011.
Wang et al., "Regulation of mature ADAM17 by redox agents for L-selectin shedding," J Immunol., 182(4):2449-2457, Feb. 15, 2009.
Warburton et al., "Treatment ofHER-2/neu overexpressing breast cancer xenograft models with trastuzumab (Herceptin) and gefitinib (ZD1839): drug combination effects on tumor growth, HER-2/neu and epidermal growth factor receptor expression, and viable hypoxic cell fraction," Clin Canc Res., 10:2512-2524.
Wiemik et al., "Targeting natural killer cells to acute myeloid leukemia in vitro with a CD16 x 33 bispecific killer cell engager and ADAM17 inhibition," Clin Cancer Res., 19(14): 3844-3855, Jul. 2013.
Wilber et al., "Efficient and stable transgene expression in human embryonic stem cells using transposon-mediated gene transfer," Stem Cells., 25(1 1):2919-2927, Nov. 2007.
Wilken et al., "Trastuzumab Sensitizes Ovarian Cancer Cells to EGFR-targeted Therapeutics," J Ovarian Res., 3:7, 2010.
Woll et al., "Human embryonic stem cells differentiate into a homogeneous population of natural killer cells with potent in vivo antitumor activity," Blood., 113:6094-6101, 2009.
Wu et al., "A novel polymorphism ofFcgammaRIIIa (CD16) alters receptor function and predisposes to autoimmune disease," J Clin Invest., 100(5):1059-1070, Sep. 1997.
Glorius et al., "The novel tribody [(CD20)2xCD16] efficiently triggers effector cell-mediated lysis of malignant B cells," Leukemia, Jun. 4, 2012, 27(1):190-201.
Mechetina et al., "Identification of CD16-2, a novel mouse receptor homologous to CD16/FcγRIII," Immunogenetics, Aug. 2, 2002, 54(7):463-468.
Extended European Search Report in European Appln. No. 22210531.4, dated Jul. 13, 2023, 10 pages.

* cited by examiner

POLYPEPTIDES, CELLS, AND METHODS INVOLVING ENGINEERED CD16

CROSS-REFERENCE TO RELATED APPLICATION

This application is a continuation of U.S. application Ser. No. 15/300,024, filed Sep. 28, 2016, which is a National Stage application under 35 U.S.C. § 371 of International Application No. PCT/US2015/022998, having an International Filing Date of Mar. 27, 2015, which claims the benefit of U.S. Provisional Ser. No. 61/971,996 filed Mar. 28, 2014. The disclosures of the prior applications are considered part of (and are incorporated by reference in) the disclosure of this application.

SUMMARY

This disclosure describes, generally, a modified form of CD16, genetically-modified cells that express the modified CD16, and methods that involve the genetically-modified cells. The modified form of CD16 can exhibit increased anti-tumor and/or anti-viral activity due, at least in part, to reduced susceptibility to metalloprotease-mediated shedding upon NK cell stimulation.

In one aspect, therefore, this disclosure describes a cell genetically modified to express a CD16 polypeptide that has a membrane proximal region and an amino acid modification in the membrane proximal region.

In another aspect, this disclosure describes a cell that includes a polynucleotide that encodes a CD16 polypeptide that has membrane proximal region and an amino acid modification in the membrane proximal region.

In either aspect, the amino acid medication reflects an addition of one or more amino acids, a deletion of one or more amino acids, or a substitution of one or more amino acids compared to the wild-type amino acid sequence of the CD16 membrane proximal region. In some of these embodiments, the substitution of one or more amino acids includes a substitution of the serine residue at position 197 of SEQ ID NO:1.

In either aspect, the cell can be a Natural Killer (NK) cell, a neutrophil, a monocyte, or a T cell.

In either aspect, the modified CD16 polypeptide exhibits reduced susceptibility to ADAM17-mediated shedding compared to a wild-type CD16 polypeptide.

In either aspect, the modified CD16 polypeptide exhibits reduced susceptibility to cleavage upon NK cell stimulation compared to a wild-type CD1 polypeptide.

In another aspect, this disclosure describes a method that generally involves administering to a patient in need of such treatment a therapy that includes (a) administering to the patient a therapeutic NK effector, and (b) administering to the patient the any embodiment of the genetically-modified cell summarized above.

In some embodiments, the therapeutic NK effector includes a therapeutic agent. In some of these embodiments, the therapeutic agent can include an antibody, or a therapeutic antibody fragment. In some of these embodiments, the antibody, or antibody fragment, specifically binds to a viral antigen. In other embodiments, the antibody, or antibody fragment, specifically binds to a tumor antigen.

In some embodiments, the therapeutic agent can include a bi-specific killer engager (BiKE) or a tri-specific killer cell engager (TriKE).

In yet another aspect, this disclosure describes a method for improving immunotherapy to a patient, in which the immunotherapy involves administering to the patient a therapeutic NK effector. Generally the method includes further administering to the patient any embodiment of the genetically-modified cell summarized above.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

This disclosure describes, generally, a modified form of CD16a, genetically-modified cells that express the modified CD16a, and methods that involve the genetically-modified cells. The modified form of CD16a can exhibit increased anti-tumor and/or anti-viral activity due, at least in part, to reduced susceptibility to metaaloprotease-mediated shedding upon NK cell stimulation.

In contrast to many solid cancer types, the survival rate of women with epithelial ovarian cancer has changed little in the last 30 years. Moreover, current standard therapies for recurrent ovarian cancer provide a low (<20%) response rate. Despite ubiquitous HER2 overexpression by ovarian cancer samples, treatment with the anti-HER2 antibody trastuzumab provides only limited responses in patients with advanced ovarian cancer. This resistance to trastuzumab may arise from dysfunctional NK cell-mediated antibody-dependent cell cytotoxicity. Thus, there is an urgent need for innovative therapeutic strategies. We describe a novel approach for providing therapeutic treatment strategy.

Figures 1, 1A:
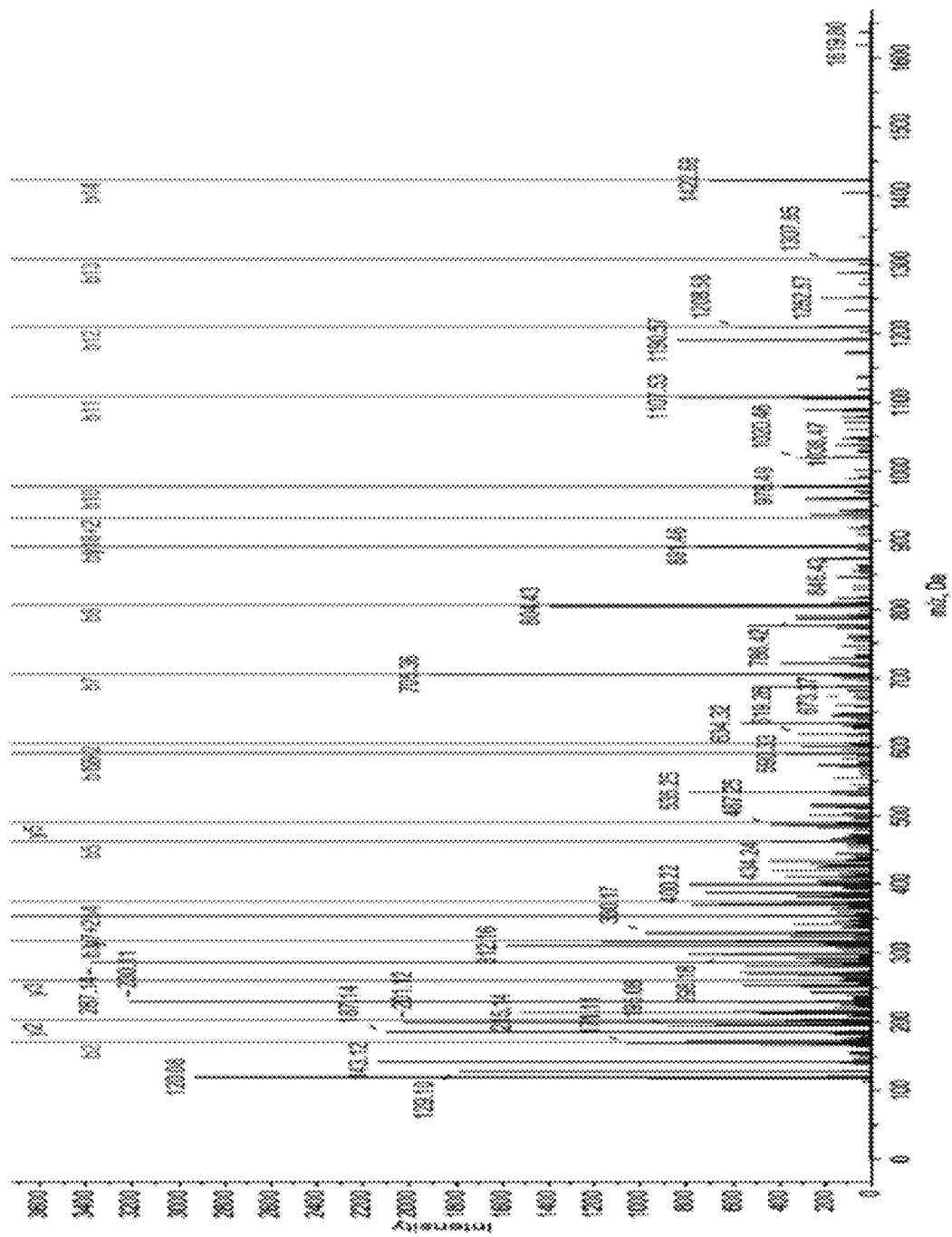
FIG. 1. Location of ectodomain cleavage sites in human CD16. (A) Tryptic peptides of soluble CD16 immunoprecipitated from the cell supernatant of PMA-activated human NK cells or neutrophils were subjected to mass spectrometry analysis. Four high confidence peptides with non-tryptic C-termini were identified: 1 peptide from soluble CD16 released by NK cells (Peptide #1, upper left) and 3 peptides from soluble CD16 released by neutrophils (Peptide #2, lower left; Peptide #3, upper right; and Peptide #4, lower right). (B) Illustration of Peptides #1-4 (underlined) and putative cleavage sites (arrowheads) in CD16a (SEQ ID NO:1) and CD16b (SEQ ID NO:2). Amino acid 176 distinguishes CD16a (F) from CD16b (V) in the identified peptides. Amino acids 1-16 indicate a predicted signal sequences of CD16a and CD16b. Amino acids 210-229 indicate the transmembrane region of CD16a. Amino acid numbering begins with methionine in the signal sequence. The amino acid sequences of CD16a and CD16b are from the NCBI reference sequences NM_000569.6 and NM_000570.4, respectively.

One concern with ovarian cancer is that the milieu in which tumor cells develop can be highly pro-inflammatory, and thus likely to promote CD16a cleavage on infiltrating NK cells and consequently diminishing antibody-dependent cell cytotoxicity. Several antibodies have emerged as effective targeted therapies for treating human malignancies. Their efficacy is due in part to antibody interactions with FcγRIIIa/CD16a on Natural Killer (NK) cells and induction of cancer cell killing by antibody-dependent cell cytotoxicity. Human IgG Fc receptor CD16 (FcγRIII) consists of two isoforms: CD16a (FcγRIIIa) and CD16b (FcγRIIIb). CD16a is expressed by Natural Killer (NK) cells and CD16b is expressed by neutrophils. NK Cell activation results in a rapid down-regulation in the surface levels of both isoforms of CD16 by a process referred to as ectodomain shedding—a proteolytic event that involves the metalloprotease ADAM17 and occurs at a single extracellular region proximal to the plasma membrane (FIG. 1A).

As noted above, ovarian cancer patients may be resistant to NK cell-mediated immunotherapies—i.e., the tumors are not sensitive to NK cell-mediated therapies. For example, ovarian cancer cells typically express the epidermal growth factor receptor HER2, yet its targeting with the therapeutic antibody trastuzumab has provided only a limited clinical response. This resistance may result, at least in part, from ectodomain shedding—i.e., NK cell activation by cytokines, target cell interaction, and/or tumor infiltration can result in CD16a cleavage and impaired antibody-dependent cell cytotoxicity. Thus, blocking the process of ectodomain shedding has clinical significance.

We have determined the cleavage sites of CD16a and CD16b using mass spectrometry and cloned the cDNAs of CD16a and CD16b from human blood leukocytes. Each cDNA was mutated in a directed manner to induce a single amino acid change. Serine at location 197 was changed to a proline. (FIG. 1B). This mutation blocks the cleavage of CD16a and CD16b, and prevents their down-regulation upon cell activation. The expression of cleavage-resistant CD16a in ex vivo expanded NK cells maintain high surface levels of this IgG Fc receptor, which enhances NK cell stimulation, the efficacy of therapeutic antibodies, and cancer call killing.

ADAM17 has a number of cell surface substrates, but possesses no consensus sequence for proteolysis that can be used to predict the site of CD16a cleavage. Therefore, we used LC-MS-MS to determine the C-terminus cleavage site in soluble CD16 released from activated human peripheral blood leukocytes. We observed three putative cleavage locations in close proximity in the membrane proximal region of CD16 (FIG. 2, arrowheads), a region that is identical between CD16a and CD16b. Although ADAM17 proteolysis does not require a consensus sequence, the secondary structure of the cleavage region is important. In an attempt to block CD16a cleavage, we substituted serine-197 with a proline (CD16a$^{197P}$) to introduce a conformational change.

We identified the location of CD16 cleavage by immunoprecipitating CD16 from the media supernatant of activated NK cells and, separately, from the media supernatant of neutrophils. The immunoprecipitated CD16 was treated with PNGaseF to remove N-glycans, trypsin digested, and the generated peptides subjected to mass spectrometric analysis. Four different peptide patterns of high confidence were identified containing non-tryptic C-termini (FIG. 1A).

For CD16 enriched from the media supernatant of activated NK cells, we observed only one peptide pattern, which corresponds to amino acids glycine-174 through alanine-195 (Peptide #1, FIG. 1A) of SEQ ID NO:1. The membrane proximal regions of CD16a and CD16b have identical amino acid sequences except for residue 176. A phenylalanine at this location is indicative of CD16a, which was present in Peptide #1 (FIGS. 1A and B). This peptide revealed a non-tryptic P1/P1' cleavage position at alanine-195/valine-196 (FIG. 1B).

For CD16 enriched from the media supernatant of activated neutrophils, we detected three different peptide patterns with non-tryptic C-termini (Peptides #2-4, FIGS. 1A and 1B). Peptide #2 corresponds to amino acids glycine-174 through alanine-195 of SEQ ID NO:2, Peptide #3 corresponds to amino acids glycine-174 through valine-196 of SEQ ID NO:2, and Peptide #4 corresponds to amino acids asparagine-180 through threonine-198 of SEQ ID NO:2. Peptide #2 and Peptide #3 contained a valine at position 176, indicative of CD16b, and revealed P1/P1' positions at alanine-195/valine-196 and at valine-196/serine-197 (FIG. 1B). Peptide #4 possessed a P1/P1' position at threonine-198/isoleucine-199 (FIG. 1B). Though this peptide was derived from soluble CD16 from enriched neutrophils, it does not contain an amino acid at position 176 to identify the isoform (FIG. 1B). Regardless, the high confidence peptide revealed a third cleavage site in CD16. Taken together, these findings demonstrate the presence of a cleavage region in CD16 rather than a single specific cleavage site.

Figures 1, 1A, 2:
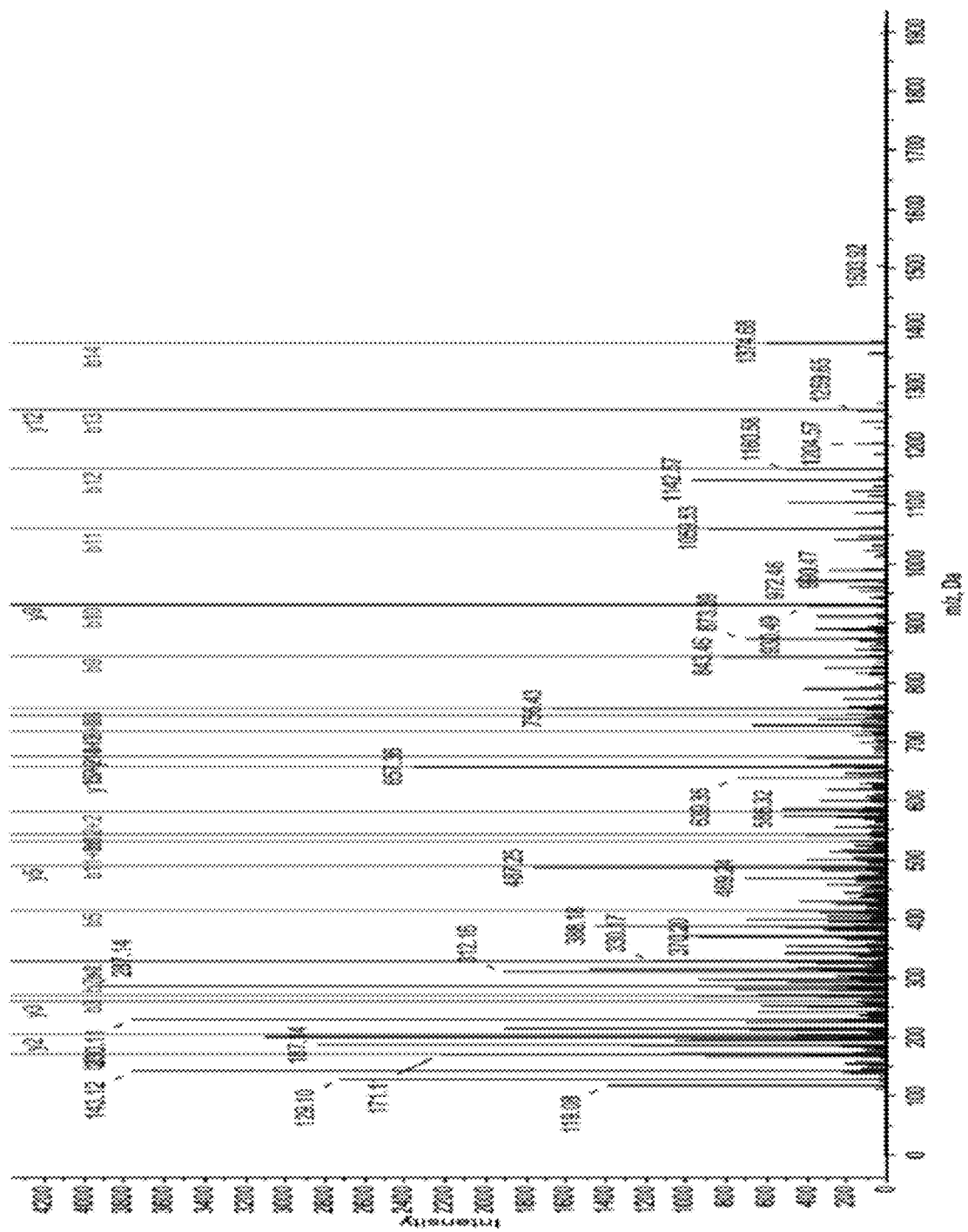
FIG. 2. Schematic illustration of CD16 ectodomain shedding, the cleavage region, and the engineered serine-197 to proline mutation. CD16a and CD16b undergo ectodomain shedding by ADAM17 within a membrane proximal region, as indicated. The CD16 cleavage region within the membrane proximal region is based on mass spectrometry analysis that revealed three distinct cleavage sites in close proximity (arrowheads). Site-directed mutagenesis was performed to substitute serine-197 in CD16 (amino acids 190-202 of SEQ ID NO:1) with a proline (CD16/S197P).

We further examined the cleavage region in CD16 by using site-directed mutagenesis to determine whether CD16a and CD16b cleavage could be disrupted in cell-based assays. ADAM17 tends to prefer an α-helical conformation in the substrate region that interacts with its catalytic site. Moreover, proteomic studies of ADAM17 cleavage site specificities revealed a very low preference for proline residues at the P1', P2', or P3' positions. We therefore substituted serine-197 in the cleavage regions of CD16a and CD16b with a proline (S197P, as indicated in FIG. 2).

Figures 1, 1A, 2, 3:
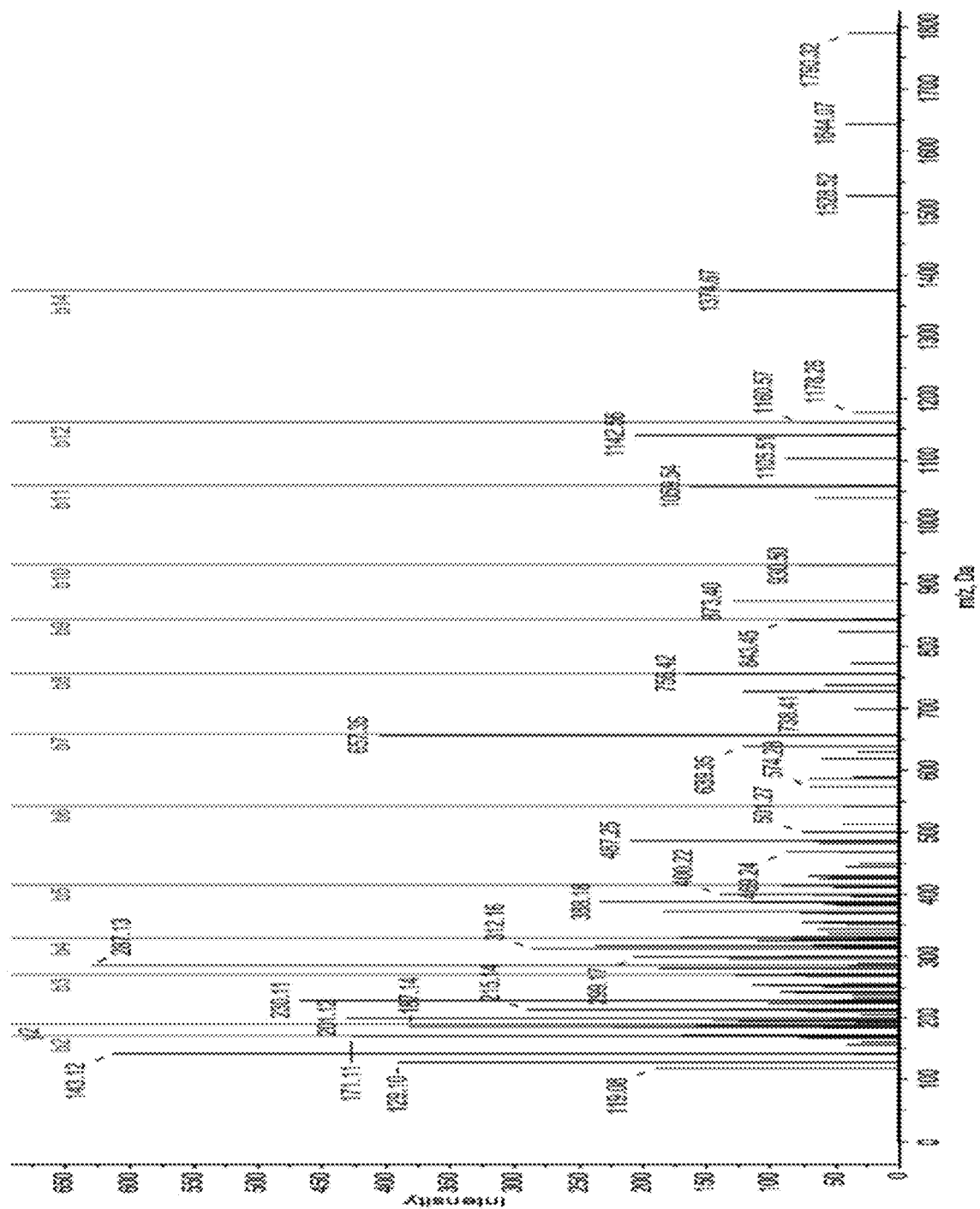
FIG. 3. Effects of the engineered S197P mutation on CD16a and CD16b shedding. Transfected HEK293 (human embryonic kidney) cells separately expressed CD16b and CD16b/S197P (A) or CD16a and CD16a/S197P (B) at similar levels, as determined by flow cytometry (left panels). The different transfectants were treated with or without PMA (15 ng/ml for 30 minutes at 37° C.) and soluble levels of CD16 in the media supernatant were quantified by ELISA (right panels). Each treatment condition was repeated three times for each experiment and the data are representative of three independent experiments. Bar graphs show mean±SD. Statistical significance is indicated as ***P<0.001. (C) Transfected HEK293 cells expressed L-selectin (CD62L) or L-selectin and CD16b/S197P. Surface levels of L-selectin and CD16b/S197P on transfected and mock-transfected cells were measured using flow cytometry (histogram plots). Transfectants expressing L-selectin or L-selectin and CD16b/S197P were incubated in the presence or absence of PMA for 30 minutes at 37° C., and the mean fluorescence intensity (MFI) of L-selectin staining determined (bar graph). Each treatment condition was repeated three times for each experiment and the data are representative of two independent experiments. Bar graphs show mean±SD. Statistical significance is indicated as *P<0.05. For all histogram plots, the x-axis=Log 10 fluorescence and the y-axis=cell number.

CD16b and CD16b/S197P were separately expressed in the human kidney cell line HEK293, which does not express endogenous CD16. The HEK293 transfectants expressed CD16b or CD16b/S197P at similar levels on their surface (FIG. 3A). High levels of CD16b were released from the transfected HEK293, which was increased further upon their treatment with PMA, as determined by ELISA (FIG. 3A). However, soluble levels of CD16b/S197P generated by untreated or PMA-treated HEK293 cells were markedly lower than those of CD16b (FIG. 3A).

We also examined the effects of the S197P mutation on CD16a cleavage using the same approach. Surface expression of CD16a requires association with γ chain dimmers. We therefore used HEK293 cells stably expressing human γ chain. Comparing HEK293 transfectants expressing equivalent surface levels of CD16a or CD16a/S197P (FIG. 3B), we determined the soluble levels of each receptor in the media supernatant of untreated and PMA-treated cells. Again, significantly lower levels of soluble CD16a/S197P were observed when compared to CD16a (FIG. 3B).

To evaluate whether the engineered S197P mutation in CD16 might disrupt ADAM17 activity, we also transfected HEK293 cells expressing or lacking CD16b/S197P with L-selectin, a well described ADAM17 substrate normally expressed by leukocytes. Both transfectants expressed equivalent levels of L-selectin, which was similarly down-regulated following their activation with PMA (FIG. 3C), demonstrating that the S197P mutation affected CD16 shedding and not ADAM17 activity.

Figures 1, 1A, 2, 3, 4:
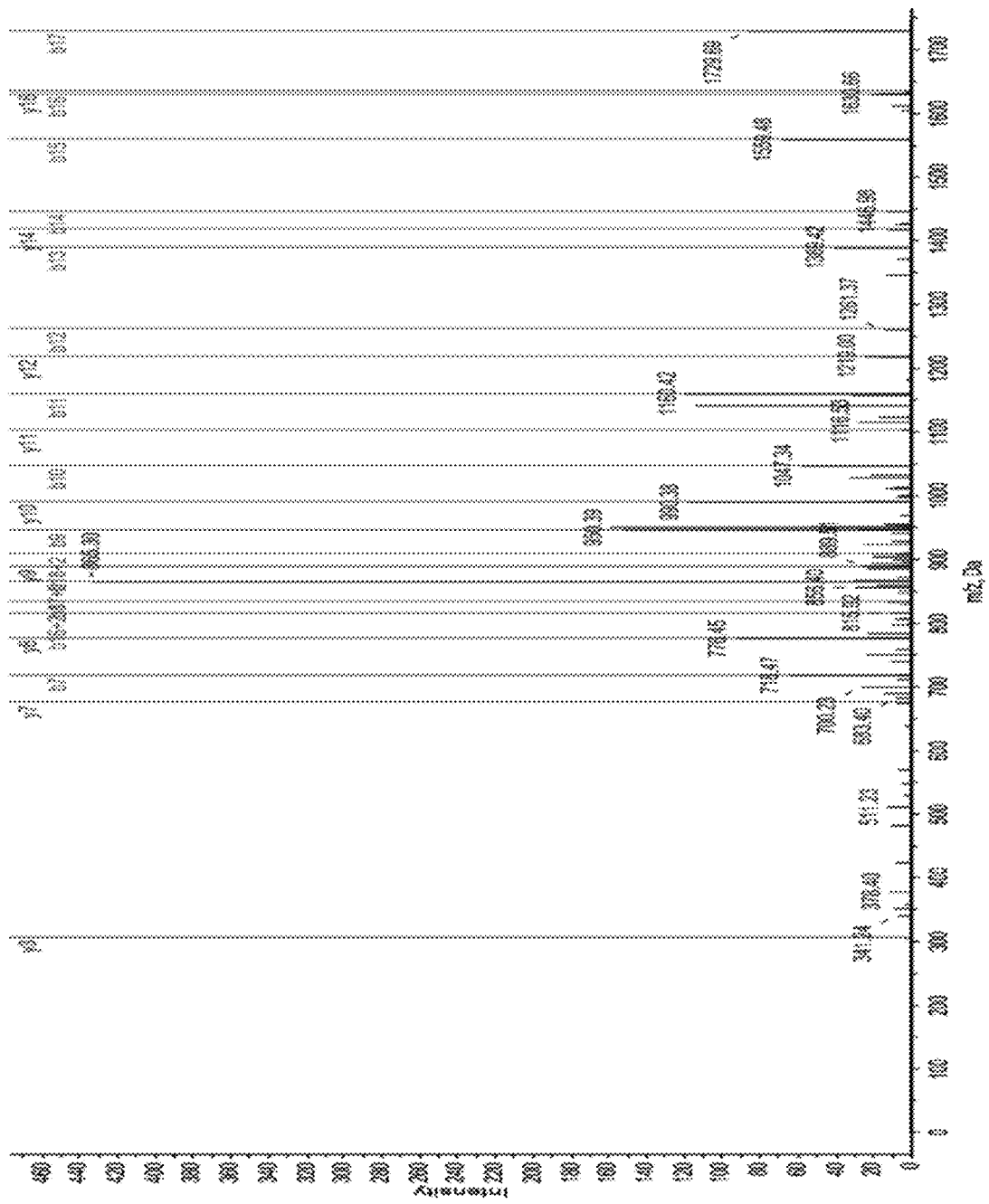
FIG. 4. Effects of the engineered S197P mutation on CD16a shedding in NK cells. NK92 cells transduced with empty vector (vector only), CD16a, or CD16a/S197P were treated without (Unstim.) or with PMA (100 ng/ml) for 30 minutes at 37° C. (A), with IL-12 and IL-18 (100 ng/ml and 400 ng/ml, respectively) for 24 hours at 37° C. (B), or with Raji cells and rituximab for 60 minutes at 37° C. (C). Cell surface levels of CD16a were determined by flow cytometry. Isotype-matched negative control antibody staining is indicated by a dotted line. (D) Parent NK92 cells and transduced cells expressing CD16a or CD16a/S197P were treated with Raji cells and rituximab in the presence or absence of the ADAM17 inhibitor BMS566394 (5 µM) for 60 minutes at 37° C. Soluble CD16a levels were determined by ELISA. Each treatment condition was repeated three times and the data are representative of three independent experiments. Bar graphs show mean±SD. Statistical significance is indicated as ***P<0.001. (E) NK92 cells expressing CD16a or CD16a/S197P were stained with the anti-ADAM17 mAbs M220, 623, 633, or an isotype-matched negative control antibody, as indicated. (F) CD56+CD45+ NK cells derived from mock-transduced iPSCs (left panel) or iPSCs expressing recombinant CD16a or CD16a/S197P (right panels) were incubated with or without K562 target cells for four hours at 37° C. For all histogram plots, the x-axis=Log 10 fluorescence, the y-axis=cell number, and the data are representative of at least 3 independent experiments.
Figure 1:
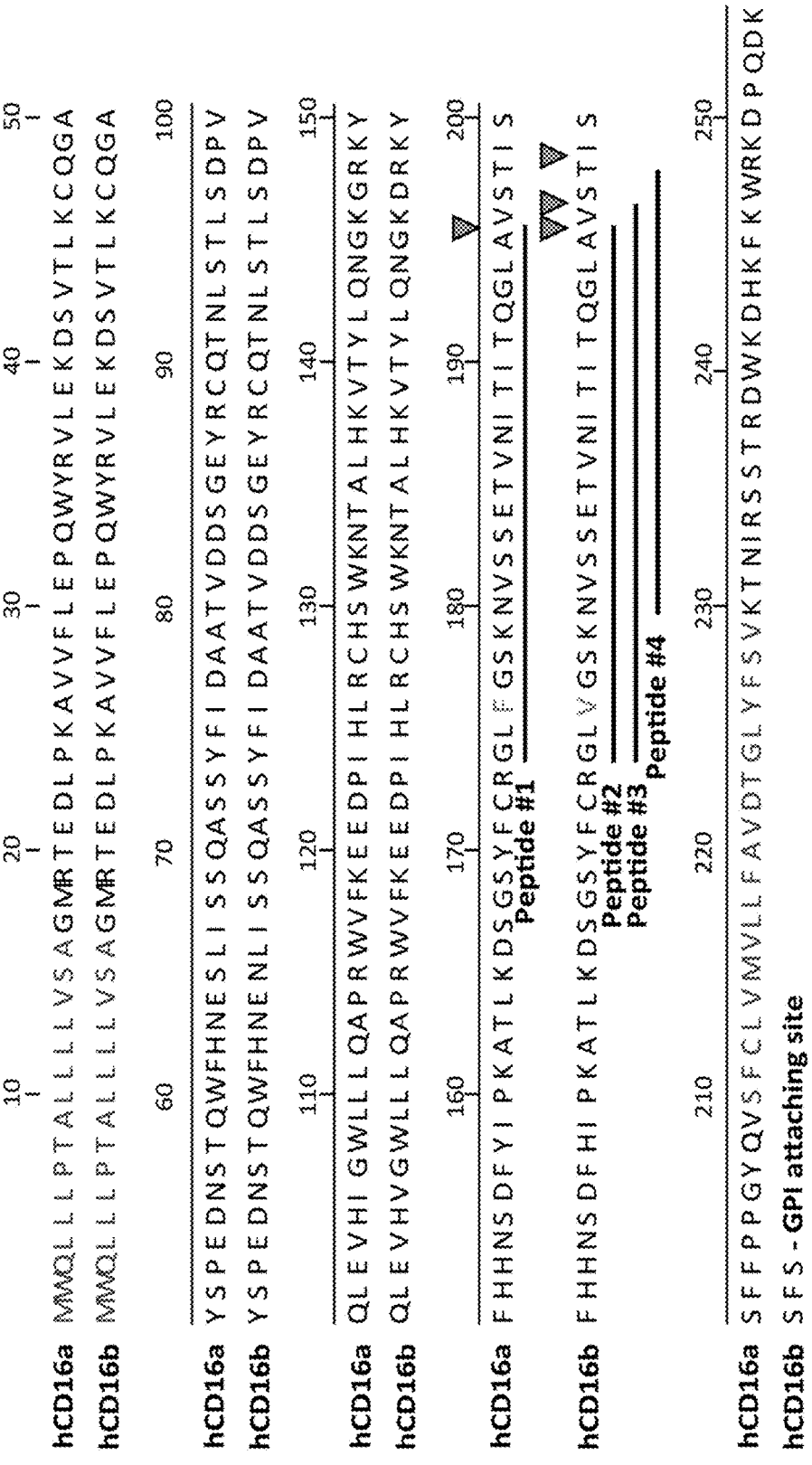
Figure 2:
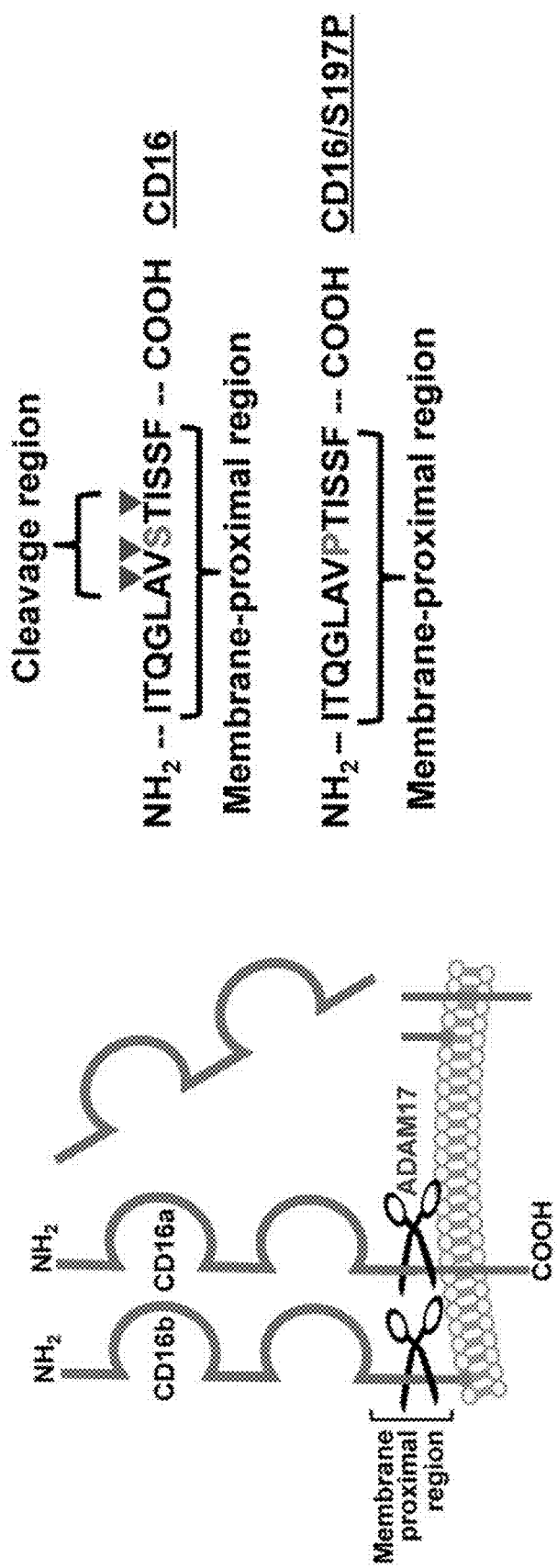
Figure 3:
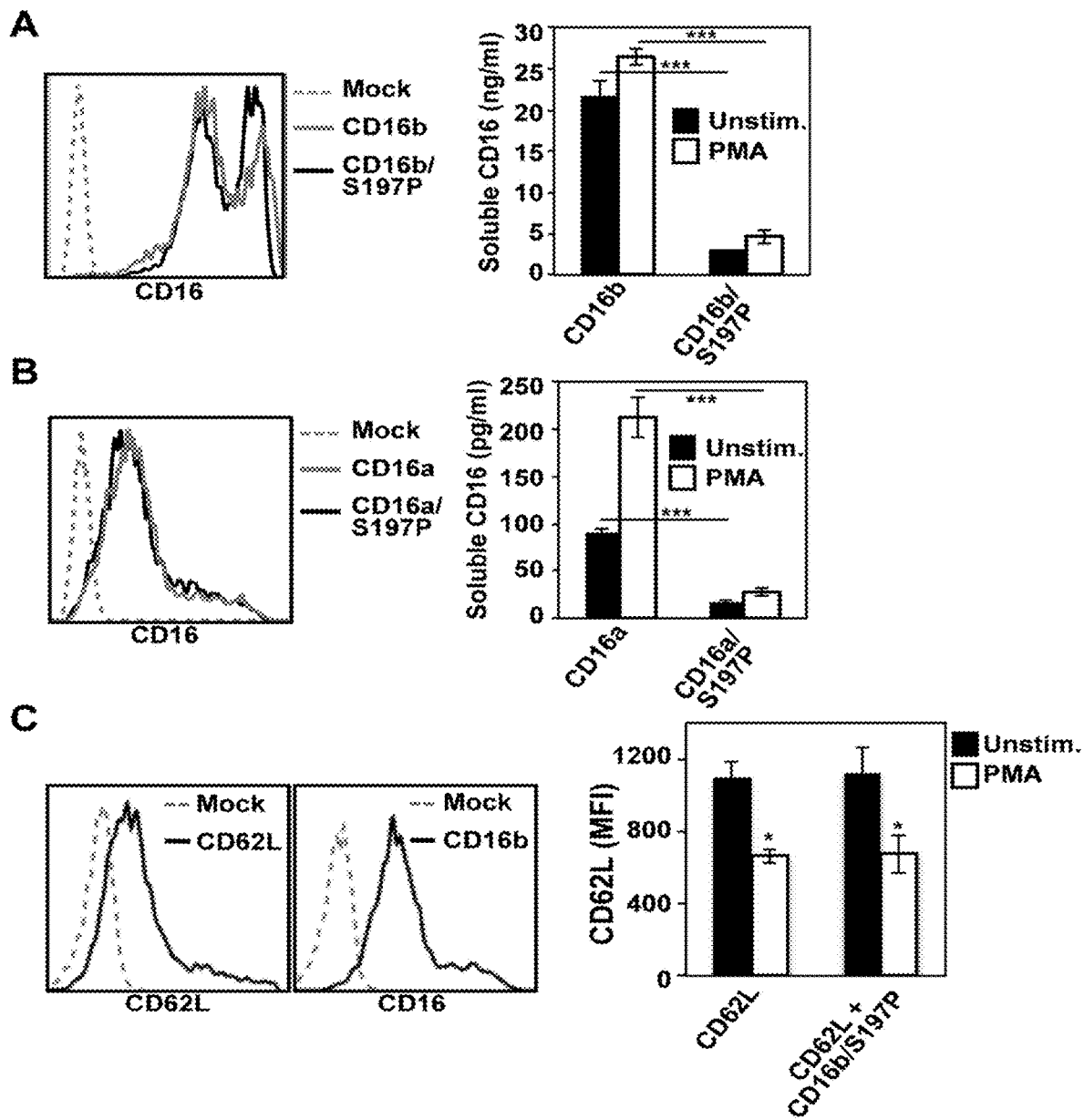
Figure 4:
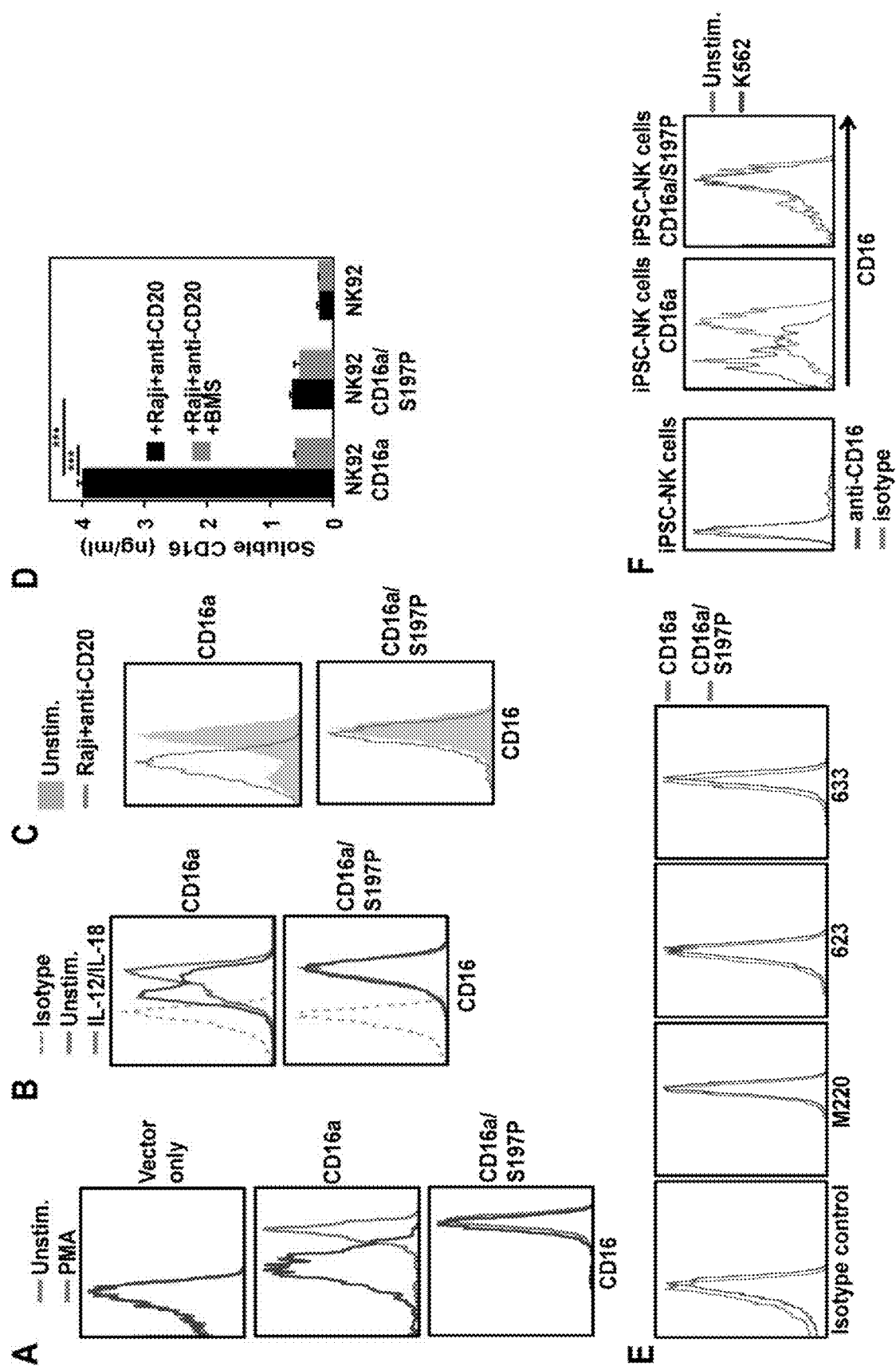

To assess the effects of the S197P mutation on CD16a shedding in NK cells, we used the human NK cell line NK92 (Gong et al., 1994, Leukemia 8:652-658). These cells lack expression of endogenous CD16a, but recombinant CD16a can be stably expressed. We transduced NK92 cells to separately express CD16a and CD16a/S197P. Cells expressing equivalent levels of these receptors were activated with PMA and cell surface CD16 levels were examined by flow cytometry. CD16a, but not CD16a/S197P, underwent a marked down-regulation in cell surface expression (FIG. 4A). IL-12 and IL-18 are physiological stimuli of NK cells that individually or in combination can induce CD16a shedding. NK92 cells treated with IL-12 and IL-18 demonstrated an appreciable down-regulation in their cell surface expression of CD16a but not CD16a/S197P (FIG. 4B). Direct engagement of cell bound IgG by CD16a also can induce its shedding, which we examined here by incubating NK92 cells expressing CD16a or CD16a/S197P with the CD20-positive Burkitt's lymphoma cell line Raji in the presence or absence of the anti-CD20 mAb rituximab. Raji cells treated with rituximab induced the down-regulation of CD16a, but not CD16a/S197P (FIG. 4C).

BMS566394 is a highly selective ADAM17 inhibitor with a potency orders of magnitude higher for ADAM17 than for other metalloproteases. BMS566394 blocked CD16a shedding with similar efficiency as the S197P mutation, but had no additional blocking effect on activated NK92 cells expressing CD16a/S197P (FIG. 4D). These findings provide further evidence that ADAM17 is the primary sheddase that cleaves CD16a within its cleavage region. It is possible, however, that ADAM17 expression levels were not equivalent in the NK92 cells expressing CD16a or CD16a/S197P, accounting for their dissimilar shedding. We therefore stained NK92 cells expressing CD16a or CD16a/S197P with multiple anti-ADAM17 mAbs and observed identical cell surface levels (FIG. 4E).

To establish the effect of the S197P mutation on CD16a shedding by primary NK cells, we used human iPSCs to generate engineered NK cells. We have previously reported on deriving functional NK cells from iPSCs and their similarity to peripheral blood NK cells (Knorr et al., 2013 Stem Cells Transl Med. 2:274-283; Ni et al., 2014, Stem Cells 32:1021-1031). CD16a and CD16a/S197P cDNA were cloned into a Sleeping Beauty transposon plasmid for gene insertion and stable expression in iPSC cells, which were subsequently differentiated into mature NK cells. NK cells derived from mock transduced iPSC cells expressed low levels of endogenous CD16a, whereas transduced CD16a and CD16a/S197P were expressed at higher levels (FIG. 4F). NK cell activation occurs through various receptors upon their interaction with K562 cells, including BY55/CD160, resulting in ADAM17 activation and CD16a shedding. We stimulated the iPSC-derived NK cells with K562 cells and found that CD16a underwent a marked down-regulation in cell surface expression, whereas the expression of CD16a/S197P remained stable (FIG. 4F).

Endogenous and recombinant CD16a have sufficient affinity to bind monomeric IgG. To examine the effects of the S197P mutation on CD16a function, we compared the IgG binding capacities of CD16a and CD16a/S197P. NK92 cells expressing CD16a or CD16a/S197P at equivalent levels bound IgG in a similar dose-dependent manner (FIG.

Figure 5:
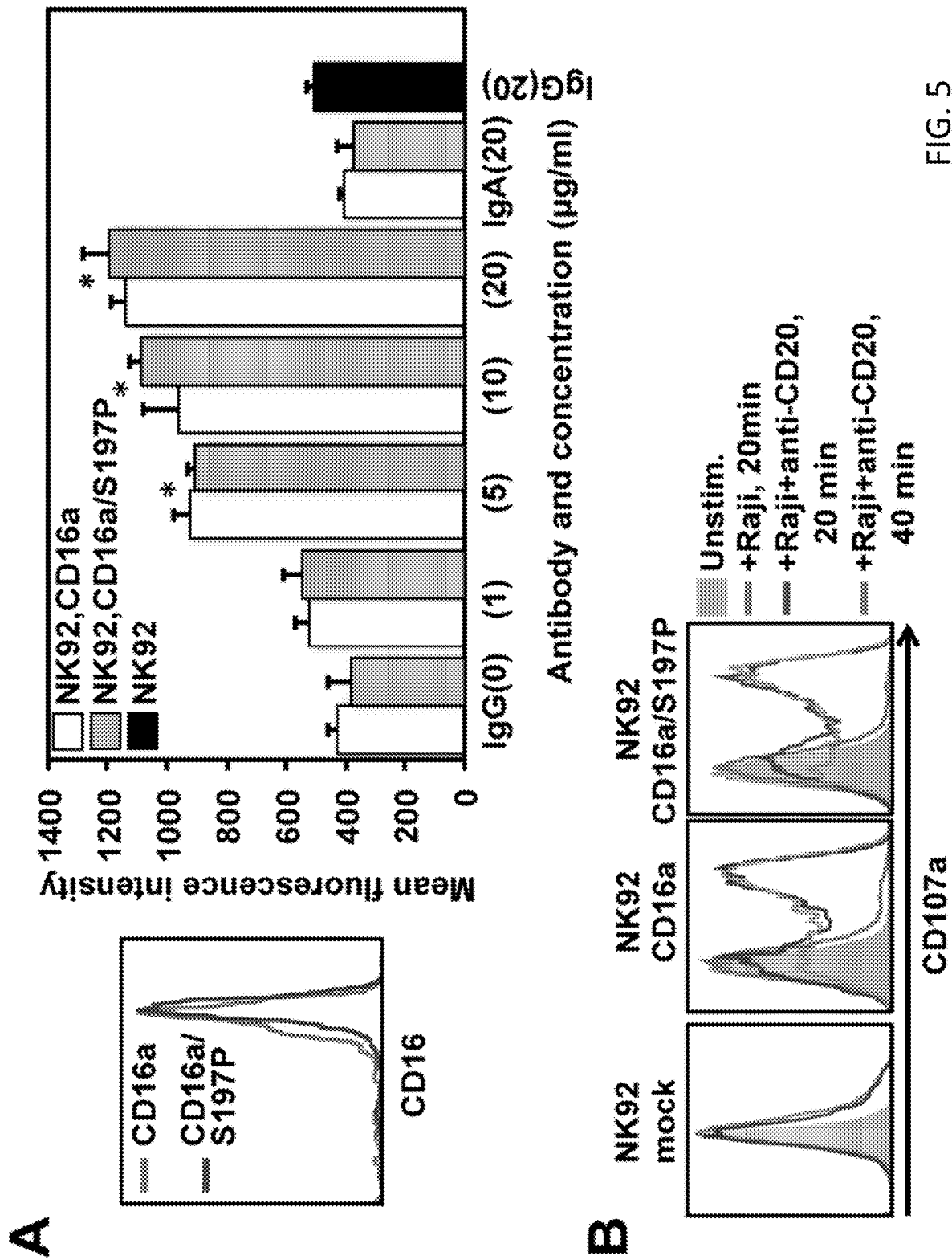
FIG. 5. Effects of the engineered S197P mutation on CD16a function. (A) NK92 cells expressing CD16a or CD16a/S197P at equivalent levels (left panel) were treated with monomeric human IgG (0-20 µg/ml). As controls, cells were also treated with monomeric human IgA (20 µg/ml), and NK92 parent cells were treated with IgG (20 µg/ml) (bar). Antibody binding was determined by flow cytometry, as described in Materials and Methods. The bar graph shows mean±SD of at least three separate experiments. Statistical significance is indicated as *P<0.05 versus IgG (0 µg/ml), IgA, or NK92 parent cells+IgG. (B) Mock transduced NK92 cells or NK92 cells expressing CD16a or CD16a/S197P were incubated in the absence (Unstim.) or presence of Raji cells treated with or without anti-CD20 rituximab for the indicated time points at 37° C. NK92 cell activation was assessed by the up-regulation in CD107a staining by flow cytometry. For the histogram plots, the x-axis=Log 10 fluorescence and the y-axis=cell number. Data are representative of at least 3 independent experiments.

5A). Controls consisted of IgA binding to NK92 cells expressing CD16a or CD16a/S197P, and IgG binding to NK92 parent cells. Both occurred at essentially background levels (FIG. 5A). These findings demonstrate specific and equivalent IgG binding by CD16a and CD16a/S197P.

CD16a is a potent activating receptor in NK cells, and we examined whether the engineered S197P mutation affected the capacity of CD16a to induce cell activation upon engagement of antibody-treated tumor cells. NK92 cell activation was assessed by measuring the up-regulation of CD107a, which occurs very rapidly upon degranulation and is a sensitive marker of NK cell activation. Mock transduced NK92 cells incubated with Raji cells treated with or without rituximab demonstrated low level and similar up-regulation CD107a (FIG. 5B). NK92 cells expressing CD16a or CD16a/S197P at equivalent levels when incubated with Raji cells alone marginally up-regulated CD107a as well, whereas their incubation with Raji cells treated with rituximab resulted in a considerable up-regulation of CD107a (FIG. 5B). Taken together, the above findings indicate that the engineered S197P mutation in CD16a did not impair its function.

Thus, we show that the engineered S197P mutation in CD16a and CD16b effectively blocked their shedding in cell-based assays that involved native ADAM17. The S197P mutation in CD16a also blocked shedding of the receptor in the human NK cell line NK92, but it did not impair receptor function. NK92 cells expressing equivalent levels of CD16a or CD16a/S197P bound monomeric IgG with similar efficiency over a range of antibody concentrations. In addition, NK92 cells expressing CD16a or CD16a/S197P up-regulated the activation marker CD107a in a comparable manner upon their engagement of rituximab bound to Raji cells.

Pluripotent stem cells allow genetic manipulation to generate engineered NK cells. This disclosure describes the generation of engineered NK cells from transduced iPSCs expressing wild-type CD16a or CD16a/S197P. As with NK92 cells, CD16a underwent shedding in the iPSCs-derived NK cells, demonstrating normal ADAM17 activity upon cell activation, whereas CD16a/S197P was not shed.

CD16a and NK cell cytotoxic function can undergo a considerable down-regulation in cancer patients. The cDNAs encoding CD16a/S197P can be used to generate stable human induced pluripotent stem cells (iPSCs) and embryonic stem cells (ESCs). These stem cells can then be differentiated into primary NK cells that express CD16a/S197P. Other cell populations that express cleavage resistant CD16a/S197P (e.g., monocytes) or CD16b/S197P (e.g., neutrophils) also can be derived from hESCs/iPSCs.

To generate an NK cell immunotherapy to be used in human patients against various forms of cancer or infection, the CD16a/S197P-expressing NK cells can mediate increased antibody-dependent cell cytotoxicity (ADCC) activity or other CD16a-mediated activity (e.g., IFNγ and TNFα production). For example, the CD16a/S197P-expressing NK cells may be combined with therapeutic antibodies (e.g., trastuzumab or rituximab), a bi-specific killer engager (BiKE, e.g., CD16×CD33, CD16×CD19, or CD16× EP-CAM bi-specific killer cell engager) or a tri-specific killer cell engager (TriKE). Other therapeutic cell populations (e.g., neutrophils, monocytes, T cells, etc.) also can be produced with increased CD16-mediated activity.

Expression of CD16a/S197P in human iPSCs or human ESCs can produce an NK cell population with enhanced ADCC activity against neoplastic conditions such as, for example, HER2 ovarian cancer. In some cases, the neoplastic condition may be treated with a therapeutic antibody such as, for example, trastuzumab. Mature NK cells may be derived from human embryonic stem cells and iPSCs.

Wild-type CD16a and/or CD16a/S197P can be cloned to generate a stable iPSC line or a stable ECS line expressing the individual CD16a receptors. Any suitable cloning method may be used. Exemplary cloning methods include, for example, viral-based methods, transposon vectors (e.g., Sleeping Beauty), or nucleofection. In one example, iPSCs may be modified using the Sleeping Beauty transposon vector. The vector can contain a selection system such as, for example, GFP/zeocin resistance fusion protein, which allows a dual selection system (zeocin resistance and flow cytometric sorting). The iPSCs can be differentiated into mature NK cells, as previously described (Ni et al., 2011, *J. Virol.* 85:43-50; Knorr et al. 2013, *Stem Cells Transl Med* 2:274-283; Woll et al., 2009, *Blood* 113:6094-6101). Expression of transgenic receptors in iPSCs can lead to a high level of expression in the derived NK cells. CD16 expression in undifferentiated iPSCs may disrupt NK cell differentiation. In such cases, CD16 expression may be delayed using, for example, a CD56 or a natural CD16a promoter, so that CD16 expression better coincides with normal NK cell differentiation.

One can compare NK cells expressing equivalent levels of wild-type CD16a versus CD16a/S197P. Expression levels of the CD16 constructs can be matched by FACS sorting based on GFP expression, which occurs in a proportional manner to the CD16 constructs. Matched CD16a levels can be verified by FACS. NK cell cytotoxicity against HER2-expressing ovarian cancer cells can be assessed by a standard chromium release assay in the presence or absence of a therapeutic antibody such as, for example, trastuzumab. Antibody-dependent cell cytotoxicity with non-chromium labeled ovarian cancer cells can be evaluated. One can evaluate NK cell production of cytokines (e.g., IFNγ, TNFα) and soluble levels of CD16a by ELISA, and the cell surface levels of CD16a and other activation markers (e.g., CD107a, CD62L) by FACS.

The human tumor xenograft model described in Example 3 can be used to evaluate the anti-cancer activity of NK cells that express non-cleavable CD16a in vivo. Unlike human CD16, mouse CD16 does not undergo ectodomain shedding upon cell stimulation, and thus determining the effects of CD16a shedding on NK cell-mediated ADCC cannot be modeled in normal mice. Table 1 provides a representative set of experimental groupings and treatments.

TABLE 1

Tumor xenograft model

| Group | n | Treatment# |
|---|---|---|
| 1 | 5 | No treatment |
| 2 | 5 | OVCAR3 cells only |
| 3 | 5 | OVCAR3 + NK cells/WT-CD16a |
| 4 | 5 | OVCAR3 + NK cells/WT-CD16a + trastuzumab |
| 5 | 5 | OVCAR3 + NK cells/CD16a$^{197P}$ |
| 6 | 5 | OVCAR3 + NK cells/CD16a$^{197P}$ + trastuzumab |
| 7 | 5 | OVCAR3 + NK cells/vector only |
| 8 | 5 | OVCAR3 + NK cells/vector + trastuzumab |

Treatment performed at least twice and data pooled.

Tumor growth and/or regression can be monitored weekly by conventional methods including, for example, bioluminescent imaging, ultrasound, CT, MRI, another imaging technology, and/or weighing the mice (Woll et al., 2009, *Blood* 113:6094-6101). Mice also can be bled (e.g., weekly) to quantify human NK cell survival. The expression and/or cell surface levels of various effector function markers (e.g., IFNγ, CD16a) can be evaluated using conventional techniques such as, for example, by FACS. Mice can be followed for any suitable period such as, for example, 60 days. At the time of sacrifice, internal organs (e.g., spleen, liver, lungs, kidney, and/or ovaries) can be examined for evidence of metastasis (e.g., by bioluminescence), as previously described (Woll et al., 2009, *Blood* 113:6094-6101).

Our analyses allow one to define and compare the antibody-dependent cell cytotoxicity activity and in vivo potency of iPSC-derived NK cells expressing wild-type CD16a versus CD16a/S197P. Thus, we describe herein a modified form of CD16a, genetically-modified cells (e.g., NK cells, neutrophils, monocytes, T cells, etc.) that express the modified CD16a, and methods that involve the genetically-modified cells. For example, NK cells expressing the modified form of CD16a, CD16a/S197P, exhibit increased anti-ovarian cancer activity due, at least in part, to reduced susceptibility to ADAM17-mediated shedding upon NK cell stimulation. This, in turn, increases antibody-dependent cell cytotoxicity activity upon engaging antibody-tagged cancer cells such as, for example, cancer cells tagged with a therapeutic antibody. Moreover, antibody recognition by NK cells increases contact stability with tumor cells and bolsters NK cell activity through other activating receptors, such as NKG2D.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Mass Spectrometry

Peripheral blood collection from healthy individuals was performed in accordance with protocols approved by the University of Minnesota Institutional Review Board according to protocol #9708M00134. Human neutrophil and NK cell isolation was performed as previously described (Wang et al., 2013, *Biochim Biophys Acta.* 1833:680-685; Long et al., 2010, *J Leukoc Biol.* 87:1097-1101; Long et al., 2012, *J Leukoc Biol.* 92:667-672). Enriched neutrophils or NK cells ($1\times10^7$/ml in PBS; Mediatech, Inc. Manassas, VA) were activated with PMA (15 ng/ml or 50 ng/ml, respectively; Sigma-Aldrich, St. Louis, MO) for 30 minutes at 37° C. Cell supernatants were filtered (0.45 µm pore size) and CD16 was immunoprecipitated using the mAb 3G8 (BioLegend, Inc., San Diego, CA) and the Pierce direct immunoprecipitation kit (Thermo Fisher Scientific, Rockford, IL), according to the manufacturer's instructions. Purified CD16 was deglycosylated by chitin binding domain-tagged Remove-iT PNGase F (New England BioLabs, Inc., Ipswich, MA), according to the manufacturer's instructions. Briefly, 10-20 µg of purified CD16 was denatured in the presence of 40 mM DTT at 55° C. for 10 minutes and then incubated with 3 µl of REMOVE-IT PNGase F (New England BioLabs, inc., Ipswich, MA) at 37° C. for one hour. REMOVE-IT PNGase F was then removed from the reaction using chitin magnetic beads.

CD16 was subjected to SDS-PAGE and gel bands corresponding to soluble CD16 were detected by a krypton fluorescent protein stain (Thermo Fisher Scientific, Rockford, IL), verified by CD16 immunoblot analysis of adjacent lanes in the same gel, and were then excised and subjected to standard in-gel digestion with trypsin. Digested peptides extracted from the gel were dried down and reconstituted for liquid chromatography-mass spectrometry analysis in 98:2: 0.01, water:acetonitrile:formic acid and ≤1 µg aliquots were analyzed by mass spectrometry (VELOS ORBITRAP, Thermo Fisher Scientific, Rockford, IL) in a data dependent scan mode, as described previously (Lin-Moshier et al., 2013, *J Biol Chem.* 288:355-367). Database searches were performed with Protein Pilot 4.5 (AB Sciex, Framingham, MA), which uses the Paragon scoring algorithm (Shilov et al., 2007, Mol Cell Proteomics 6:1638-1655), against the NCBI reference sequence *Homo sapiens* protein FASTA database to which the contaminant database (thegpm.org/cRAP/index, 109 proteins) was appended. Search parameters were: cysteine iodoacetamide; trypsin; instrument Orbi. MS (1-3 ppm) Orbi MS/MS; biological modifications ID focus, which includes asparagine deamidation; a thorough search effort; and False Discovery Rate analysis (with reversed database).

Generation of cDNA Expression Constructs

CD16b occurs as two allelic variants termed NA1 and NA2, differing by four amino acids in the N-terminal portion of its extracellular region. Both allelic variants of CD16b are cleaved with similar efficiency by ADAM17. For this study, we examined only the NA1 variant. There are also two allelic variants of CD16a that have either a valine or phenylalanine residue at position 176. These two allelic variants of CD16a were cleaved with similar efficiency by ADAM17. For this study, we examined only the valine allelic variant CD16a.

CD16a and CD16b were amplified from human leukocyte cDNA, separately cloned into the pcDNA3.1 plasmid (Invitrogen, Carlsbad, CA) at the BamHI and EcoRI restriction enzyme sites as previously described (Wang et al., 2013, *Biochim Biophys Acta.* 1833:680-685; Dong et al., 2014, *Arthritis Rheumatol.* 66:1291-1299). The constructs were then subjected to Quik-Change Site-directed Mutagenesis (Agilent Technologies, Santa Clara, CA) according to the manufacturer's instructions to convert the serine at position 197 to a proline in CD16a and CD16b. All constructs were sequenced to confirm the presence of the intended mutation and the absence of any spontaneous mutations.

The CD16a cDNA was subsequently cloned into the bi-cistronic retroviral expression vector pBMN-IRES-EGFP, provided by Dr. G. Nolan (Stanford University, Stanford, CA), at the BamHI and EcoRI restriction enzyme sites. The CD16a constructs were also cloned into a bicistronic Sleeping Beauty transposon plasmid (pKT2-IRES-GFP:zeo) as previously described (Wilber et al., 2007, *Stem Cells* 25:2919-2927; Tian et al., 2009, *Stem Cells* 27:2675-2685). Briefly, wild-type CD16a and CD16a/S197P were PCR amplified using the primers: 5'-CCG GAA TTC CAG TGT GGC ATC ATG TGG CAG CTG CTC-3' (sense, SEQ ID NO:XX) and 5'-CCG GAA TTC TCA TTT GTC TTG AGG GTC CTT TCT-3' (antisense, SEQ ID NO:YY). EcoRI sites are underlined. The EcoRI-digested CD16a and CD16a/S197P PCR fragments were separately cloned into pKT2-IRES-GFP:zeo. Correct CD16a orientation and sequence were confirmed by PCR and sequencing analyses. We have previously cloned full-length human L-selectin (CD62L) cDNA (Feehan et al., 1996, *J Biol Chem.* 271: 7019-7024; Matala et al., 2001, *J Immunol.* 167:1617-1623), which was transferred to the pcDNA3.1 vector at the restriction enzyme site XbaI. Full-length human FcRγ cDNA was cloned as previously described (Dong et al., 2014, *Arthritis Rheumatol.* 66:1291-1299), with the modification that a pcDNA3.1 vector was used.

Generation of Cell Lines Expressing Recombinant L-Selectin, CD16a, and CD16b

HEK293 cells (a human embryonic kidney cell line) and NK92 cells (a human NK cell line) (ATCC, Manassas, VA) were cultured according to the depository's instructions. HEK293 cells were transiently transfected with pcDNA3.1 with or without CD16b, CD16b/S197P, and/or L-selectin using Lipofectamine 2000 (Invitrogen, Carlsbad, CA) according to the manufacturer's instructions. HEK293 cells stably expressing human FcRγ were transiently transfected with pcDNA3.1 with or without CD16a or CD16a/S197P by the same approach. NK92 cells were stably transduced with pBMN-IRES-EGFP with or without CD16a or CD16a/S197P by retrovirus generation and infection procedures described previously (Matala et al., 2001, *J Immunol.* 167: 1617-1623; Walcheck et al., 2003, *J Leukoc Biol.* 74:389-394; Wang et al., 2009, *J Immunol.* 182:2449-2457). Construct expression was assessed by EGFP fluorescence and CD16 staining, as determined by flow cytometry. Human iPSCs (UCBiPS7, derived from umbilical cord blood CD34 cells) were maintained on mouse embryonic fibroblasts (Knorr et al., 2013, *Stem Cells Transl Med.* 2:274-283; Ni et al., 2014, *Stem Cells* 32:1021-1031). Stable expression of CD16a or CD16a/S197P was performed using a Sleeping Beauty transposon system as previously described (Wilber et al., 2007, *Stem Cells* 25:2919-2927; Tian et al., 2009, *Stem Cells* 27:2675-2685). Briefly, iPSCs were nucleofected with pKT2-IRES-GFP:zeo in combination with transposase DNA in nucleofector solution V (Lonza Inc., Gaithersburg, MD) using program setting B16. Nucleofected cells were immediately suspended in iPSC growth medium containing zeocin (50 µg/ml) and seeded onto mouse embryonic fibroblasts.

NK Cell Derivation from CD16a-hESC and CD16a-iPSC Cells

Hematopoietic differentiation of hESCs and iPSCs was performed as previously described (Ng et al., 2005, *Blood* 106: 1601-1603; Ng et al., 2008, *Nat Protoc* 3:768-776; Le Garff-Tavernier et al., 2010, *Aging Cell* 9: 527-535). Briefly, 3000 single cells were seeded per well of 96-well round bottom plates in BPEL media with stem cell factor (SCF, 40 ng/ml), vascular endothelial growth factor (VEGF, 20 ng/ml) and bone morphogenic protein 4 (BMP4, 20 ng/ml). BPEL media contained Iscove's Modified Dulbecco's Medium (IMDM, 86 ml, Invitrogen, Thermo Fisher Scientific, Inc., Waltham. MA), F12 Nutrient Mixture with Glutmax I (86 mL, Invitrogen, Thermo Fisher Scientific, Inc., Waltham. MA), 10% deionized Bovine Serum Albumin (BSA, 5 ml, Sigma-Aldrich, St. Louis, MO), 5% Polyvinyl alcohol (10 ml, Sigma-Aldrich, St. Louis, MO), linolenic acid (20 µl of 1 gm/ml solution, Sigma-Aldrich, St. Louis, MO), linoleic acid (20 µl of 1 gm/ml solution, Sigma), SYNTHECOL 500× solution (Sigma-Aldrich, St. Louis, MO), a-monothioglyceral (3.9 µl/100 ml, Sigma-Aldrich, St. Louis, MO), Protein-free hybridoma mix II (Invitrogen, Thermo Fisher Scientific, Inc., Waltham. MA), ascorbic acid (5 mg/ml, Sigma), GLUTAMAX I (Invitrogen, Thermo Fisher Scientific, Inc., Waltham. MA), Insulin-transferrin-selenium 100× solution (Invitrogen, Thermo Fisher Scientific, Inc., Waltham. MA), Penicillin/streptomycin (Invitrogen, Thermo Fisher Scientific, Inc., Waltham. MA).

At day 11 of hematopoietic differentiation, spin embryoid bodies were directly transferred into 24-well plates with or without EL08-1D2 stromal cells in NK media supplied with cytokines (Le Garff-Tavernier et al., 2010, *Aging Cell* 9:527-535). After 4-5 weeks of culture, single cell suspensions were stained with APC-, PE-, FITC- and PerCP-cy5.5-coupled IgG or specific antibodies against human blood surface antigens: CD45-PE, CD56-APC, CD56-PE, CD16-PerCP-cy5.5, NKG2D-PE, NKp44-PE, NKp46-PE, CD158b-FITC, CD158e1/2-FITC (BD Pharmingen, San Jose, CA), CD158a/h-PE and CD158i-PE (Beckman Coulter, Inc., Pasadena, CA). Antibody stains were assessed by flow cytometry.

Cell Stimulation

HEK293 and NK92 cells in RPMI 1640 media (Mediatech, Inc., Manassas, VA) were activated with 15 ng/ml and 100 ng/ml, respectively, PMA for 30 minutes at 37° C. NK92 cells were activated with IL-12 (PeproTech Inc, Rocky Hill, NJ) and IL-18 (R&D Systems, Inc., Minneapolis, MN) at 100 ng/ml and 400 ng/ml, respectively, for the indicated time points. NK92 cell activation through CD16a was mediated by their incubation with the CD20-positive Burkitt's lymphoma cell line Raji (ATCC, grown according to the depository's instructions) (1:1 ratio) treated with the anti-CD20 mAb rituximab (1 µg/ml) (Genentech, Inc., South San Francisco, CA), as described previously (Romee et al., 2013, *Blood* 121:3599-3608). Excess rituximab was removed by washing the Raji cells. In some experiments, NK92 cells were pre-incubated for 30 minutes with the selective ADAM17 inhibitor BMS566394 (5 µM) (Bristol-Myers Squibb Company, Princeton, NJ). NK cells derived from iPSCs were stimulated with the human erythroleukemic cell line K562 (ATCC, grown according to the depository's instructions), as previously described (Romee et al., 2013, *Blood* 121:3599-3608). Briefly, iPSC-derived NK cells were incubated with K562 target cells (2:1 ratio) for four hours at 37° C.

Antibody Binding Assay

Cell binding to monomeric human IgG and IgA (Sigma-Aldrich, St. Louis, MO) was performed as previously described with some modifications (Dong et al., 2014, *Arthritis Rheumatol.* 66:1291-1299). NK92 parent cells or transduced cells expressing CD16a or CD16a/S197P at 5×10$^6$/ml in PBS were incubated with IgG or IgA at the indicated concentrations in triplicate for one hour at 4° C. The cells were extensively washed and incubated with APC-conjugated donkey anti-human Fc (heavy and light chain) antibody (Jackson Immunoresearch, West Grove, PA) according to the manufacturer's instructions. The cells were washed and then immediately analyzed by flow cytometry.

Flow Cytometry and ELISA

For cell staining, nonspecific antibody binding sites were blocked and cells were stained with the indicated antibodies and examined by flow cytometry, as previously described (Wang et al., 2013, *Biochim Biophys Acta.* 1833:680-685; Romee et al., 2013, *Blood* 121:3599-3608). Flow cytometric analysis was performed on FACSCanto and LS RH instruments (BD Biosciences, San Jose, CA). Human CD16 was detected by the mAbs 3G8 (BioLegend, Inc., San Diego, CA) and DJ130c (Santa Cruz Biotech, Santa Cruz, CA). CD107a was detected by the mAb H4A3 (Biolegend, Inc., San Diego, CA). ADAM17 was detected by the mAbs M220 (Doedens et al., 2000, *J Biol Chem.* 275:14598-14607), 111633, and 111623 (R&D Systems, Inc., Minneapolis, MN). Human L-selectin was detected by the mAb LAM1-116 (Ancell Corp., Stillwater, MN). Isotype-matched negative control mAbs were used to evaluate levels of nonspecific staining. The CD16 ELISA was performed by a custom cytometric bead assay, as previously described (Wang et al., 2013, *Biochim Biophys Acta.* 1833:680-685).

Statistical Analysis

Statistical analysis was performed using Prism software (GraphPad, San Diego, CA) using ANOVA and student's t test where appropriate. A p value of <0.05 was considered significant.

Example 2

Comparison of NK Cells Expressing Equivalent Levels of WT CD16a and CD16a$^{197P}$ (CD16a/S197P)

Expression levels of the CD16 constructs are matched by FACS sorting based on GFP expression (as done for NK92 cells described above, FIG. 2), which occurs in a proportional manner to the CD16 constructs. Matched CD16a levels are verified by FACS for all assays. As a control, iPSC-derived NK cells modified with empty Sleeping Beauty transposon vector (expressing only GFP) are evaluated. iPSC-derived NK cells express low levels of endogenous CD16a (data not shown). NK cell cytotoxicity against HER2-expressing ovarian cancer cells is assessed by a standard chromium release assay in the presence or absence of trastuzumab. Antibody-dependent cell cytotoxicity with non-chromium labeled ovarian cancer cells is also performed. NK cell production of cytokines (e.g., IFNγ, TNFα) and soluble levels of CD16a are evaluated by ELISA. Cell surface levels of CD16a and other activation markers (e.g., CD107a, CD62L) are evaluated by FACS.

Example 3

Human tumor xenograft model for testing whether iPSC-derived NK cells expressing CD16a$^{197P}$ (CD16a/S197P) have increased in vivo anti-ovarian cancer activity in the presence of trastuzumab.

A xenograft model using NOD/SCID/γc$^{-/-}$ (NSG) mice and human ovarian cancer cell lines stably engineered to express firefly luciferase for bioluminescent imaging (Geller et al., 2013, *Cytotherapy* 15:1297-1306) is used to test intraperitoneal (ip) delivery of NK cell activity against ovarian cancer cells. The OVCAR3 ovarian cancer cell line, which over-expresses HER2, is used as the in vivo target (Hellstrom et al., 2001, *Cancer Res* 61:2420-2423). Sublethally-irradiated (225 cGY) NSG female mice are injected intraperitoneally with OVCAR3 (2×10$^5$ cells) generated to express luciferase for bioluminescent imaging to quantify tumor growth or regression (Geller et al., 2013, *Cytotherapy* 15:1297-1306). Tumors are allowed to grow for seven days before the mice get a single intraperitoneal injection of 20×10$^6$ NK cells. Mice are then given IL-2 (5 μg/mouse) every other day for four weeks as previously described (Woll et al., 2009, *Blood* 113: 6094-6101) to promote in vivo survival of NK cells. Trastuzumab is administered at a dose of 50 μg intraperitoneally once weekly for four weeks, a previously used dose in this model (Warburton et al., 2004, *Clinical cancer research* 10:2512-2524). The in vivo potency of iPSC-derived NK cells expressing equivalent levels of WT CD16 or CD16a$^{197P}$ (CDa6a/S197P) are compared. Controls include iPSC-derived NK cells expressing GFP alone (vector only), and a cohort of mice receiving ovarian cancer cells only. All mice get the same IL-2 treatment.

Tumor growth/regression are monitored weekly by bioluminescent imaging and weighing the mice, as previously described (Woll et al., 2009, *Blood* 113: 6094-6101). Mice are also bled weekly to quantify human NK cell survival. The expression/cell surface levels of various effector function markers (e.g., IFNγ, CD16a) are evaluated by FACS. Mice are followed for ~60 days. At the time of sacrifice, internal organs (spleen, liver, lungs, kidney, and ovaries) are examined by bioluminescence for evidence of metastasis, as previously described (Woll et al., 2009, *Blood* 113: 6094-6101).

EXEMPLARY EMBODIMENTS

Embodiment 1. A cell genetically modified to express a CD16 polypeptide that comprises a membrane proximal region and an amino acid modification in the membrane proximal region.

Embodiment 2. A cell comprising:
  a polynucleotide that encodes a CD16 polypeptide that comprises a membrane proximal region and an amino acid modification in the membrane proximal region.

Embodiment 3. The cell of Embodiment 1 or Embodiment 2 wherein the amino acid medication reflects an addition of one or more amino acids, a deletion of one or more amino acids, or a substitution of one or more amino acids compared to the wild-type amino acid sequence of the CD16 membrane proximal region.

Embodiment 4. The cell of Embodiment 3 wherein the substitution of one or more amino acids comprises a substitution of the serine residue at position 197 of SEQ ID NO:1.

Embodiment 5. The cell of any preceding Embodiment wherein the cell is a Natural Killer (NK) cell.

Embodiment 6. The cell of any preceding Embodiment wherein the cell is a neutrophil.

Embodiment 7. The cell of any preceding Embodiment wherein the cell is a monocyte.

Embodiment 8. The cell of any preceding Embodiment wherein the modified CD16 polypeptide exhibits reduced susceptibility to ADAM17-mediated shedding compared to a wild-type CD16 polypeptide.

Embodiment 9. The cell of any preceding Embodiment wherein the modified CD16 polypeptide exhibits reduced susceptibility to cleavage upon NK cell stimulation compared to a wild-type CD16 polypeptide.

Embodiment 10. A method comprising administering to a patient in need of such treatment a therapy that comprises:
  administering to the patient a therapeutic NK effector; and
  administering to the patient the cell of any one of claims 1-9.

Embodiment 11. The method of Embodiment 10 wherein the therapeutic NK effector comprises a therapeutic agent.

Embodiment 12. The method of Embodiment 11 wherein the therapeutic agent specifically recognizes a tumor antigen.

Embodiment 13. The method of Embodiment 12 wherein the therapeutic agent comprises an antibody or an antibody fragment that specifically recognizes the tumor antigen.

Embodiment 14. The method of Embodiment 13 wherein the tumor antigen comprises HER2.

Embodiment 15. The method of Embodiment 13 or Embodiment 14 wherein the antibody to comprises trastuzumab or rituximab.

Embodiment 16. The method of Embodiment 10 wherein the therapeutic NK effector comprises a bi-specific killer engager (BiKE)

Embodiment 17. The method of Embodiment 16 wherein the BiKE comprises a CD16×CD33 BiKE, a CD16×CD19 BiKE, or a CD16×EP-CAM BiKE.

Embodiment 18. The method of Embodiment 10 wherein the therapeutic NK effector comprises a tri-specific killer cell engager (TriKE).

Embodiment 19. The method of any one of Embodiments 11 or 16-18 wherein the therapeutic agent specifically recognizes a viral target.

Embodiment 20. A method for improving therapy to a patient that includes administering to the patient a therapeutic NK effector, the method comprising:

administering to the patient the cell of any one of claims 1-9.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

What is claimed is:

1. An in vitro method of modifying a human cell, comprising:
introducing into a human cell an exogenous polynucleotide encoding a human CD16a polypeptide comprising S197P (CD16a/S197P), wherein expression of the human CD16a polypeptide in a human NK cell is effective to improve antibody-dependent cell cytotoxicity as compared to a counterpart human NK cell expressing a respective wild type human CD16 polypeptide of SEQ ID NO: 1 or SEQ ID NO:2.

2. The in vitro method of claim 1, wherein the modified human cell exhibits at least one characteristic selected from the group consisting of:
(a) increased anti-tumor capability;
(b) increased anti-viral capability;
(c) increased IFNγ or TNFα production;
(d) increased CD16a-mediated activity;

(e) higher cell surface level of CD16a;
(f) lower level of soluble CD16a;
(g) enhanced cell stimulation; and
(h) increased in vivo anti-cancer activity,
as compared to a counterpart unmodified human cell that does not comprise said exogenous polynucleotide.

3. The in vitro method of claim 1, wherein said modified human cell is a hematopoietic cell.

4. The in vitro method of claim 1, wherein said modified human cell is a natural killer (NK) cell, a neutrophil, or a T cell.

5. The in vitro method of claim 1, wherein said modified human cell is a pluripotent stem cell.

6. The in vitro method of claim 1, wherein said CD16a/S197P further comprises a valine residue at position 176 (176V).

7. The in vitro method of claim 1, wherein said human cell is a pluripotent stem cell, and wherein said introducing step further comprises:
(i) engineering said pluripotent stem cell by contacting said pluripotent stem cell with said polynucleotide, thereby obtaining an engineered pluripotent stem cell; and
(ii) directing differentiation of said engineered pluripotent stem cell to a differentiated cell, wherein said differentiated cell expresses said polypeptide encoded by said exogenous polynucleotide, thereby obtaining a modified human cell having improved antibody-dependent cell cytotoxicity.

8. The in vitro method of claim 7, wherein said differentiated cell exhibits at least one characteristic selected from the group consisting of:
(a) increased anti-tumor capability;
(b) increased anti-viral capability;
(c) increased IFNγ or TNFα production;
(d) increased CD16a-mediated activity;
(e) higher cell surface level of CD16a;
(f) lower level of soluble CD16a;
(g) enhanced cell stimulation; and
(h) increased in vivo anti-cancer activity,
as compared to a counterpart cell that does not have said exogenous polynucleotide.

9. The in vitro method of claim 7, wherein said differentiated cell is a hematopoietic cell.

10. The in vitro method of claim 7, wherein said differentiated cell is a natural killer (NK) cell, a neutrophil, or a T cell.

11. The in vitro method of claim 7, wherein said pluripotent stem cell is an iPSC (induced pluripotent stem cell).

12. The in vitro method of claim 7, wherein said CD16a/S197P further comprises a valine residue at position 176 (176V).

13. The in vitro method of claim 7, wherein said pluripotent stem cell comprising said exogenous polynucleotide does not express said encoded polypeptide.

14. The in vitro method of claim 7, wherein said pluripotent stem cell comprising said exogenous polynucleotide expresses said encoded polypeptide.

15. The in vitro method of claim 1, wherein the human CD16a polypeptide detectably binds antibody 3G8.

16. A composition comprising a population of modified human cells generated according to the method of claim 1, and one or more therapeutic antibodies.

17. A composition comprising a population of modified human cells generated according to the method of claim 7, and one or more therapeutic antibodies.

18. The in vitro method of claim 4, wherein said modified human cell is differentiated from a genetically engineered pluripotent stem cell, and wherein the engineered pluripotent stem cell comprises the polynucleotide encoding the human CD16a polypeptide.

* * * * *

SEQUENCE LISTING

```
<160> NUMBER OF SEQ ID NOS: 2

<210> SEQ ID NO 1
<211> LENGTH: 254
<212> TYPE: PRT
<213> ORGANISM: Homo sapiens

<400> SEQUENCE: 1

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140
```

```
Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
        210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 2
<211> LENGTH: 203
<212> TYPE: PRT
<213> ORGANISM: Homo sapiens

<400> SEQUENCE: 2

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Asn Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Val Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser
        195                 200
```